(12) United States Patent
Yang et al.

(10) Patent No.: US 9,393,314 B2
(45) Date of Patent: Jul. 19, 2016

(54) MELOXICAM EYE DROPS AND PREPARATION METHOD AND USE THEREOF

(71) Applicant: KANGYA OF NINGXIA PHARMACEUTICALS CO., LTD., Yinchuan, Ningxia (CN)

(72) Inventors: Yajun Yang, Yinchuan (CN); Zhonggui He, Yinchuan (CN); Yimeng Qin, Yinchuan (CN)

(73) Assignee: KANGYA OF NINGXIA PHARMACEUTICALS CO., LTD, Yinchuan, Ningxia (CN)

( * ) Notice: Subject to any disclaimer, the term of this patent is extended or adjusted under 35 U.S.C. 154(b) by 0 days.

(21) Appl. No.: 14/773,191

(22) PCT Filed: Oct. 28, 2013

(86) PCT No.: PCT/CN2013/086042
§ 371 (c)(1),
(2) Date: Sep. 4, 2015

(87) PCT Pub. No.: WO2014/134922
PCT Pub. Date: Sep. 12, 2014

(65) Prior Publication Data
US 2016/0022822 A1    Jan. 28, 2016

(30) Foreign Application Priority Data
Mar. 7, 2013  (CN) .......................... 2013 1 0072193

(51) Int. Cl.
| | | |
|---|---|---|
| A61K 47/40 | (2006.01) | |
| A61K 31/5415 | (2006.01) | |
| A61K 9/00 | (2006.01) | |
| A61K 47/32 | (2006.01) | |
| A61K 47/36 | (2006.01) | |
| A61K 47/38 | (2006.01) | |
| A61K 47/02 | (2006.01) | |

(52) U.S. Cl.
CPC ............... *A61K 47/40* (2013.01); *A61K 9/0048* (2013.01); *A61K 31/5415* (2013.01); *A61K 47/02* (2013.01); *A61K 47/32* (2013.01); *A61K 47/36* (2013.01); *A61K 47/38* (2013.01)

(58) Field of Classification Search
CPC ...................................................... A61K 47/40
USPC ........................................................ 514/226.5
See application file for complete search history.

(56) References Cited

FOREIGN PATENT DOCUMENTS

| | | |
|---|---|---|
| CN | 1301177 A | 6/2001 |
| CN | 1493292 A | 5/2004 |
| CN | 103110575 A | 5/2013 |
| EP | 0 033 042 B1 * | 8/1984 |
| EP | 1082066 A1 | 3/2001 |

OTHER PUBLICATIONS

Cashman et al., Dermatitis (2005), vol. 16(2), pp. 57-66.*
Ya-nan Wang et al., "Research and Application of Hydroxypropyl-beta-cyclodextrin in Pharmaceutics" Food and Drug, vol. 9(4): 47-50, 2007.
Ru-Lin Wang et al., "The Enhanced Solubility of Oxicams through Inclusion by β-cyclodextrin and Its Derivatives" Chinese J. of Spectroscopy Laboratory, vol. 25(5):959-962, 2008.

* cited by examiner

*Primary Examiner* — Taofiq A Solola
(74) *Attorney, Agent, or Firm* — McCarter & English, LLP; Danielle L. Herritt; Mei Bai

(57) ABSTRACT

Disclosed are meloxicam eye drops and the preparation method and use thereof. The eye drops contain active ingredient meloxicam or a pharmaceutically acceptable salt thereof, a solubilizer, a stabilizer, a pH adjusting agent, an antimicrobial agent and an osmotic pressure adjusting agent, wherein the solubilizer is one of hydroxypropyl-β-cyclodextrin, sulfobutylether-β-cyclodextrin, and β-cyclodextrin or a mixture thereof, and the stabilizer is one of polymer povidone, sodium hyaluronate, and hypromellose or a mixture thereof.

8 Claims, No Drawings

MELOXICAM EYE DROPS AND PREPARATION METHOD AND USE THEREOF

CROSS-REFERENCE TO RELATED APPLICATIONS

This application is a 35 U.S.C. §371 national stage filing of International Application No. PCT/CN2013/086042, filed on Oct. 28, 2013, which claims priority to Chinese Patent Application No. 201310072193.7, filed on Mar. 7, 2013. Each of the foregoing applications is incorporated herein by reference in its entirety.

TECHNOLOGY FIELD

The present invention relates to pharmaceutical technology, in particular relates to a meloxicam eye drop, and the preparation method and use thereof.

BACKGROUND ART

Meloxicam (4-hydroxy-2-methyl-N-(5-methyl-2-thiazolyl)-2H-1,2-benzothiazine-3-carboxamide-1,1-dioxide) is a new generation non-steroidal anti-inflammatory drug, which has strong pharmacological effects like anti-inflammation, analgesia, antipyresis etc. It is the first marketed COX-2 inhibitor. However, studies suggest that there exists metabolic polymorphism on the in vivo pharmacokinetic behavior of meloxicam in Chinese subjects. It is probably caused by the variation in the degree of first-pass metabolism in the Chinese, but overall slow metabolism is the major type. If certain injection is administered in combination with oral medication at the early stage of treatment to rapidly reach the peak concentration, significant effects will be achieved in improving therapeutic effect and alleviating the patients' suffering. On the other hand, the anti-inflammatory effects of eye drops made from non-steroidal anti-inflammatory drugs are exactly the same with those of topically applied corticosteroid eye drops, and the non-steroidal anti-inflammatory drugs have strong ocular permeability in eyes; while the side effects of long-term use of corticosteroid can be avoided. A prior patent (publication No. CN1301177A) disclosed that meloxicam can be used for treating ocular inflammation, and it suggested that meloxicam eye drops have excellent effects. However, the formulation provided by that patent contains surfactants such as Tween-80; due to the limitations from the intrinsic nature of the surfactants, there is concern about its dosage and safety.

Cyclodextrin (CD) is a new pharmaceutical excipient, which can clathrate various pharmaceutical active ingredients at the molecular level, therefore impart them new physical and chemical properties, wherein the characteristic of increasing the solubility of the insoluble and poorly soluble drugs makes cyclodextrin attract much attention in the area of liquid pharmaceutical preparations. Among them, hydroxypropyl-β-cyclodextrin (HP-β-CD), which is a hydroxyalkyl derivative of β-CD, is the first intravenously injectable β-CD derivative approved by FDA in US. The itraconazole injection containing HP-β-CD produced by Johnson & Johnson has been marketed. The sulfobutylether-β-cyclodextrin (SBE-β-CD) developed by Cydex Corp., US in 1990s is the product of substitution reaction between β-CD and 1,4-butane sultone. An antipsychotic agent named Ziprasidone injection, which has SBE-β-CD as the clathrate material, has been successfully developed by Pfizer and marketed in the U.S. The two cyclodextrins show promising applications in the preparation of liquid medicine.

Due to their significant advantages, polymers are preliminarily replacing the surfactants in the area of liquid preparation for external use. It prevents the potential toxicity, irritation, hemolysis and other side effects of the surfactants, and also greatly contributes to improving the solubility and stability of the drugs. At the same time, the particular viscosity of polymers has special significance to the eye drops. It may not only reduce the irritation, but also increase the residence time of the drug solution in the eyes.

SUMMARY OF THE INVENTION

The invention provides a meloxicam eyedrop, the preparation method and application thereof, which overcome the limitations in the prior art, moreover, it provides liquid preparation with better stability, higher safety and better tolerance.

The problems to be solved in the present invention are solved through the following technical solutions:

A meloxicam eye drop, characterized in that it contains active ingredient meloxicam or a pharmaceutically acceptable salt thereof, a solubilizer, a stabilizer, an osmotic pressure regulator and optional bacteriostatic agent; the solubilizer is one of hydroxypropyl-β-cyclodextrin, sulfobutylether-β-cyclodextrin, and β-cyclodextrin or a mixture thereof; the stabilizer is one of polymer povidone, sodium hyaluronate, and hydroxypropyl methyl cellulose (HPMC) or a mixture thereof.

The pharmaceutically acceptable salt of meloxicam is diethylamine salt, methylglucamine salt, sodium salt, potassium salt or ammonium salt. Diethylamine salt is preferred.

The meloxicam eye drops consist of the following components in terms of weight: meloxicam or its pharmaceutically acceptable salts, 0.05%-2.0%; solubilizer, 1.0-10%; stabilizer, 0.1-10%; pH regulator, 0.1-8.0%; osmotic pressure regulator, 0.1-2.0%; bacteriostatic agent, 0-0.5%; water for injection, 85-98%.

Preferably, the meloxicam eye drops consist of the following components in terms of weight: meloxicam or its pharmaceutically acceptable salts, 0.05%-2.0%; solubilizer, 1.0-10%; stabilizer, 0.1-10%; pH regulator, 0.1-8.0%; osmotic pressure regulator, 0.1-2.0%; and water for injection as balance.

wherein meloxicam or its pharmaceutically acceptable salts is preferably 0.1%, the solubilizer is preferably hydroxypropyl-β-cyclodextrin of 1.0%-5%, the stabilizer is preferably hydroxypropyl methyl cellulose of 0.1-2%. Moreover, the weight ratio of hydroxypropyl-β-cyclodextrin to hydroxypropyl methyl cellulose is preferably 5:1-1:2.

The pH regulator is one of hydrochloric acid, boric acid, borax, sodium dihydrogen phosphate, disodium hydrogen phosphate, potassium dihydrogen phosphate, citric acid, and sodium citrate or a mixture thereof.

The osmotic pressure regulator is one of sodium chloride, potassium chloride, boric acid, borax, sodium sulfate, potassium sulfate, sodium nitrate, potassium nitrate, sodium acetate, mannitol, glycerol, propylene glycol, and glucose or a composition of two or more; wherein sodium chloride and glucose are preferred.

The bacteriostatic agent is one of methyl paraben, ethyl paraben, propyl paraben, butyl paraben, benzalkonium chloride, benzalkonium bromide, chlorhexidine acetate, phenylmercuric nitrate, and thimerosal or a mixture thereof;

The pH of meloxicam eye drops is 6.5-9.0, preferably 7.5-8.5.

The method for preparing meloxicam eye drops, comprising: dissolving the solubilzer in certain amount of water; adding and completely dissolving meloxicam or its pharmaceutically acceptable salts under heating and stirring; sequentially adding other excipients, stirring till completely dissolved; cooling the solution to room temperature; adjusting the pH, adding water for injection to full amount; filtering with microporous filter membrane.

Use of meloxicam eye drops in the treatment of non-infectious ophthalmic inflammation.

Based on the physical and chemical properties of meloxicam itself, and considering the current status in the development of new type cyclodextrins, the inventors use constant temperature accelerated test as evaluation means. It was found that the excellent properties of the two types of cyclodextrin in promoting solubilization and increasing stability of the drugs still apply to meloxicam, and through the comparison with the non-aqueous solvent group, the addition of cyclodextrin not only substituted the addition of non-aqueous solvent and the surfactants but also, solubilization of the drugs can be achieved through adding only small amount of cyclodextrin, therefore the requirements for medical use can be satisfied, while the stability is significantly improved. The results are shown in table 1, wherein in formulation 1 PEG400 is selected as solubilizer and stabilizer for meloxicam eye drops, while in formulations 2 and 3, cyclodextrin is added as solubilizer and stabilizer for meloxicam eye drops.

TABLE 1

The effect of various solubilizers on the stability of meloxicam eye drops

| Group | t0.9(day) |
| --- | --- |
| PEG400 | 125 |
| hydroxypropyl-β-cyclodextrin (formulation 2) | 4774 |
| sulfobutylether-β-cyclodextrin (formulation 3) | 4689 |

In the study of meloxicam eye drops, in order to investigate the influence of polymers on the effect of cyclodextrin in solubilization and stability improvement, the polymers were added into above formulations 2 and 3, respectively. Unexpectedly, it was found that the stability of the solution was greatly improved. The results are shown in Table 2.

TABLE 2

The effect of HPMC on the stability of eye drops containing meloxicam and cyclodextrin

| Group | t0.9(day) |
| --- | --- |
| control | 199 |
| formulation 2 HPMC added | 8830 |
| formulation 3 HPMC added | 8789 |

More specifically, the present invention relates to a solution type preparation containing meloxicam, which overcomes the limitations in prior art. Through the test and investigation, the superior, promising novel excipients are perfectly combined with the drugs for the first time, therefore a liquid preparation with better stability, safety and tolerance is provided. At the same time, the special functions of conventional excipients and new excipients were found, while a breakthrough in improving the stability of the liquid preparation is achieved.

DESCRIPTION OF EMBODIMENTS

Example 1

Prepare 0.1% meloxicam eye drops containing 1% HP-β-CD and 0.1% HPMC as solubilizer and stabilizer.

| Ingredient | Formulation amount (g) | Percentage (%) |
| --- | --- | --- |
| meloxicam | 0.1 | 0.1 |
| HP-β-CD | 1 | 1 |
| HPMC | 0.1 | 0.1 |
| borax | 3.0 | 3.0 |
| boric acid | 1.2 | 1.2 |
| ethyl paraben | 0.03 | 0.03 |
| sodium chloride | 0.43 | 0.43 |
| water for injection | Add to 100 mL | |

Preparation method: the formulation amount of HP-β-CD was weighed and dissolved in 90 mL of water for injection. Borax and boric acid were added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 2

Prepare 0.1% meloxicam eye drops containing 5% HP-β-CD and 0.1% HPMC as solubilizer and stabilizer.

| Ingredient | Formulation amount (g) | Percentage (%) |
| --- | --- | --- |
| meloxicam | 0.1 | 0.1 |
| HP-β-CD | 5 | 5 |
| HPMC | 0.1 | 0.1 |
| borax | 3.0 | 3.0 |
| boric acid | 1.2 | 1.2 |
| sodium chloride | 0.43 | 0.43 |
| water for injection | Add to 100 mL | |

Preparation method: the formulation amount of HP-β-CD was weighed and dissolved in 90 mL of water for injection. Borax and boric acid were added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 3

Prepare 0.1% meloxicam eye drops containing 5% HP-β-CD and 0.1% sodium hyaluronate as solubilizer and stabilizer.

| Ingredient | Formulation amount (g) | Percentage (%) |
| --- | --- | --- |
| meloxicam | 0.1 | 0.1 |
| HP-β-CD | 5 | 5 |
| sodium hyaluronate | 0.1 | 0.1 |

-continued

| Ingredient | Formulation amount (g) | Percentage (%) |
|---|---|---|
| Na$_2$HPO$_4$ | 0.76 | 0.76 |
| NaH$_2$PO$_4$ | 0.16 | 0.16 |
| ethyl paraben | 0.03 | 0.03 |
| sodium chloride | 0.43 | 0.43 |
| water for injection | Add to 100 mL | |

Preparation method: the formulation amount of HP-β-CD was weighed and dissolved in 90 mL of water for injection. Na$_2$HPO$_4$, NaH$_2$PO$_4$ were added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 4

Prepare 0.1% meloxicam eye drops containing 10% HP-β-CD and 0.1% sodium hyaluronate as solubilizer and stabilizer.

| Ingredient | Formulation amount (g) | Percentage (%) |
|---|---|---|
| meloxicam | 0.1 | 0.1 |
| HP-β-CD | 10 | 10 |
| sodium hyaluronate | 0.1 | 0.1 |
| boric acid | 1.0 | 1.0 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filter with 0.22 μm microporous filter membrane, finally aliquoted into the sealed plastic bottles.

Example 5

Prepare 0.1% meloxicam eye drops containing 10% HP-β-CD and 1% sodium hyaluronate as solubilizer and stabilizer.

| Ingredient | Formulation amount (g) | Percentage (%) |
|---|---|---|
| meloxicam | 0.1 | 0.1 |
| HP-β-CD | 10 | 10 |
| sodium hyaluronate | 1.0 | 1 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 6

Prepare 0.1% meloxicam eye drops containing 10% HP-β-CD and 10% sodium hyaluronate as solubilizer and stabilizer.

| Ingredient | Formulation amount (g) | Percentage (%) |
|---|---|---|
| meloxicam | 0.1 | 0.1 |
| HP-β-CD | 10 | 10 |
| sodium hyaluronate | 10 | 10 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 7

Prepare 0.1% meloxicam eye drops containing 10% HP-β-CD and 0.45% hydroxypropyl methyl cellulose as solubilizer and stabilizer.

| Ingredient | Formulation amount (g) | Percentage (%) |
|---|---|---|
| meloxicam | 0.1 | 0.1 |
| HP-β-CD | 10 | 10 |
| hydroxypropyl methyl cellulose | 0.45 | 0.45 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 8

Prepare 0.1% meloxicam eye drops containing 10% HP-β-CD and 1% hydroxypropyl methyl cellulose as solubilizer and stabilizer.

| Ingredient | Formulation amount (g) | Percentage (%) |
| --- | --- | --- |
| meloxicam | 0.1 | 0.1 |
| HP-β-CD | 10 | 10 |
| hydroxypropyl methyl cellulose | 1 | 1 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 9

Prepare 0.1% meloxicam eye drops containing 10% HP-β-CD and 2% hydroxypropyl methyl cellulose as solubilizer and stabilizer.

| Ingredient | Formulation amount (g) | Percentage (%) |
| --- | --- | --- |
| meloxicam | 0.1 | 0.1 |
| HP-β-CD | 10 | 10 |
| hydroxypropyl methyl cellulose | 2 | 2 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 10 prepare 0.1% meloxicam eye drops containing 5% HP-β-CD and 2% hydroxypropyl methyl cellulose as solubilizer and stabilizer.

| Ingredient | Formulation amount (g) | Percentage (%) |
| --- | --- | --- |
| meloxicam | 0.1 | 0.1 |
| HP-β-CD | 5 | 5 |
| hydroxypropyl methyl cellulose | 2 | 2 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 11

Prepare 0.1% meloxicam eye drops containing 5% HP-β-CD and 1% hydroxypropyl methyl cellulose as solubilizer and stabilizer.

| Ingredient | Formulation amount (g) | Percentage (%) |
| --- | --- | --- |
| meloxicam | 0.1 | 0.1 |
| HP-β-CD | 5 | 5 |
| hydroxypropyl methyl cellulose | 1 | 1 |
| boric acid | 1.0 | 1 |
| benzalkonium bromide | 0.02 | 0.02 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Example 12

Prepare 0.1% meloxicam eye drops containing 1% HP-β-CD and 2% hydroxypropyl methyl cellulose as solubilizer and stabilizer.

| Ingredient | Formulation amount (g) | Percentage (%) |
| --- | --- | --- |
| meloxicam | 0.1 | 0.1 |
| HP-β-CD | 1 | 1 |
| hydroxypropyl methyl cellulose | 2 | 2 |
| boric acid | 1.0 | 1 |
| sodium chloride | 0.31 | 0.31 |
| water for injection | Add to 100 mL | |

Preparation method: the formulation amount of HP-β-CD was weighed and dissolved in 90 mL of water for injection. Boric acid was added and dissolved. The solution was heated to 80° C. in water bath. Then 0.1 g meloxicam was added to the solution and stirred; after completely dissolved, other excipients were added sequentially, and continued to stir till completely dissolved. After adjusting pH to 7.5, water for injection was added to the final volume of 100 mL. Then the solution was filtered with 0.22 μm microporous filter membrane, finally aliquoted into the sealed plastic bottles.

Comparative Example 1

| | |
|---|---|
| Meloxicam | 0.50 g |
| Hydro xypropyl-β-cyclodextrin (HP-β-CD) | 16.65 g |
| Sodium Hydroxide | 0.335 g |
| Boric Acid | 5.0 g |
| Benzalkonium Bromide | 0.1 g |
| Sodium chloride | 1.55 g |
| water for injection | Add to 500 mL |

Preparation method: the formulation amount of boric acid and HP-β-CD were weighed and dissolved in 90 mL water for injection. The solution was heated to 80° C. in water bath. Then 0.5 g meloxicam was added to the solution and stirred; after completely dissolved, other excipients were added sequentially, and continued to stir till completely dissolved. After adjusting pH to 7.5, water for injection was added to the final volume of 500 mL. Then the solution was filtered with 0.22 μm microporous filter membrane, finally aliquoted into the sealed plastic bottles.

Comparative Example 2

| | |
|---|---|
| Meloxicam | 0.50 g |
| Sodium Hydroxide | 0.335 g |
| Boric Acid | 5.0 g |
| Benzalkonium Bromide | 0.1 g |
| Sodium chloride | 1.55 g |
| water for injection | Add to 500 mL |

Preparation method: the formulation amount of sodium hydroxide was weighed and dissolved in 40 mL water for injection. The solution was heated to 80° C. in water bath. Then 0.5 g meloxicam was added to the solution and stirred; after completely dissolved, other excipients were added sequentially, and continued to stir till completely dissolved. After adjusting pH to 7.5, water for injection was added to the final volume of 500 mL. Then the solution was filtered with 0.22 μm microporous filter membrane, finally aliquoted into the sealed plastic bottles.

Test Method for Stability of the Eye Drops Prepared in Examples and Comparative Examples:

1. Influencing Factors Test

The meloxicam eye drops prepared in above Examples and Comparative Examples were taken and placed into colorless, transparent and sealed ampoules, stored under the conditions of a temperature of 60° C. and 4500Lx±500Lx of illumination respectively, sampled for inspection on the 5th and 10th day, the results were compared with those from the 0th day sample. The test results are shown in Table 5, Table 6:

TABLE 5

Test results of influencing factor of 60° C. on meloxicam eye drops

| Condition | Sample | Time (days) | Appearance | pH value | Content (%) | Related substances % |
|---|---|---|---|---|---|---|
| High temperature 60° C. | Example 1 | 0 | Light yellow-green clear liquid | 7.7 | 100.0 | 0.41 |
| | | 5 | Light yellow-green clear liquid | 7.7 | 98.9 | 0.85 |
| | | 10 | Light yellow-green clear liquid | 7.7 | 97.6 | 1.03 |
| | Example 2 | 0 | Light yellow-green clear liquid | 7.7 | 100.0 | 0.42 |
| | | 5 | Light yellow-green clear liquid | 7.7 | 99.3 | 0.54 |
| | | 10 | Light yellow-green clear liquid | 7.7 | 98.5 | 0.79 |
| | Example 3 | 0 | Light yellow-green clear liquid | 7.7 | 100.0 | 0.41 |
| | | 5 | Light yellow-green clear liquid | 7.7 | 99.9 | 0.51 |
| | | 10 | Light yellow-green clear liquid | 7.7 | 99.1 | 0.74 |
| | Example 4 | 0 | Light yellow-green clear liquid | 7.7 | 100.0 | 0.41 |
| | | 5 | Light yellow-green clear liquid | 7.7 | 99.6 | 0.79 |
| | | 10 | Light yellow-green clear liquid | 7.7 | 99.1 | 0.96 |
| | Example 5 | 0 | Light yellow-green clear liquid | 7.7 | 100.0 | 0.41 |
| | | 5 | Light yellow-green clear liquid | 7.7 | 99.9 | 0.59 |
| | | 10 | Light yellow-green clear liquid | 7.7 | 99.7 | 0.83 |
| | Example 6 | 0 | Light yellow-green clear liquid | 7.7 | 100.0 | 0.41 |
| | | 5 | Light yellow-green clear liquid | 7.7 | 99.8 | 0.47 |
| | | 10 | Light yellow-green clear liquid | 7.7 | 99.7 | 0.58 |
| | Example 7 | 0 | Light yellow-green clear liquid | 7.7 | 100.0 | 0.41 |
| | | 5 | Light yellow-green clear liquid | 7.7 | 99.7 | 0.55 |
| | | 10 | Light yellow-green clear liquid | 7.7 | 99.4 | 0.67 |
| | Example 8 | 0 | Light yellow-green clear liquid | 7.7 | 100.0 | 0.41 |
| | | 5 | Light yellow-green clear liquid | 7.7 | 99.9 | 0.52 |
| | | 10 | Light yellow-green clear liquid | 7.7 | 99.7 | 0.59 |
| | Example 9 | 0 | Light yellow-green clear liquid | 7.7 | 100.0 | 0.41 |
| | | 5 | Light yellow-green clear liquid | 7.7 | 99.9 | 0.49 |
| | | 10 | Light yellow-green clear liquid | 7.7 | 99.7 | 0.55 |
| | Example 10 | 0 | Light yellow-green clear liquid | 7.7 | 100.0 | 0.41 |
| | | 5 | Light yellow-green clear liquid | 7.7 | 99.9 | 0.50 |
| | | 10 | Light yellow-green clear liquid | 7.7 | 99.7 | 0.64 |
| | Example 11 | 0 | Light yellow-green clear liquid | 7.7 | 100.0 | 0.41 |
| | | 5 | Light yellow-green clear liquid | 7.7 | 99.1 | 0.63 |
| | | 10 | Light yellow-green clear liquid | 7.7 | 98.4 | 0.85 |

TABLE 5-continued

Test results of influencing factor of 60° C. on meloxicam eye drops

| Condition | Sample | Time (days) | Appearance | pH value | Content (%) | Related substances % |
|---|---|---|---|---|---|---|
| | Example 12 | 0 | Light yellow-green clear liquid | 7.7 | 100.0 | 0.40 |
| | | 5 | Light yellow-green clear liquid | 7.7 | 99.4 | 0.53 |
| | | 10 | Light yellow-green clear liquid | 7.7 | 99.3 | 0.61 |
| | Comparative Example 1 | 0 | Light yellow-green clear liquid | 7.7 | 100.0 | 0.41 |
| | | 5 | Light yellow-green clear liquid | 7.7 | 99.0 | 0.88 |
| | | 10 | Light yellow-green clear liquid | 7.7 | 98.4 | 1.35 |
| | Comparative Example 2 | 0 | Light yellow-green clear liquid | 7.7 | 100.0 | 0.41 |
| | | 5 | Light yellow-green clear liquid | 7.7 | 98.5 | 1.25 |
| | | 10 | Light yellow green clear liquid | 7.7 | 97.2 | 2.15 |

TABLE 6

Test results of influencing factor of illumination on meloxicam eye drops

| Condition | Sample | Time (days) | Appearance | pH value | Content (%) | Related substances % |
|---|---|---|---|---|---|---|
| illumination (4500Lx ± 500Lx) | Example 1 | 0 | Light yellow-green clear liquid | 7.7 | 100.0 | 0.41 |
| | | 5 | Light yellow-green clear liquid | 7.7 | 98.2 | 1.06 |
| | | 10 | Light yellow-green clear liquid | 7.7 | 97.6 | 1.87 |
| | Example 2 | 0 | Light yellow-green clear liquid | 7.7 | 100.0 | 0.40 |
| | | 5 | Light yellow-green clear liquid | 7.7 | 98.9 | 0.84 |
| | | 10 | Light yellow-green clear liquid | 7.7 | 98.4 | 1.15 |
| | Example 3 | 0 | Light yellow-green clear liquid | 7.7 | 100.0 | 0.41 |
| | | 5 | Light yellow-green clear liquid | 7.7 | 99.1 | 0.79 |
| | | 10 | Light yellow-green clear liquid | 7.7 | 98.8 | 0.98 |
| | Example 4 | 0 | Light yellow-green clear liquid | 7.7 | 100.0 | 0.41 |
| | | 5 | Light yellow-green clear liquid | 7.7 | 98.4 | 0.99 |
| | | 10 | Light yellow-green clear liquid | 7.7 | 97.6 | 1.68 |
| | Example 5 | 0 | Light yellow-green clear liquid | 7.7 | 100.0 | 0.41 |
| | | 5 | Light yellow-green clear liquid | 7.7 | 99.0 | 0.74 |
| | | 10 | Light yellow-green clear liquid | 7.7 | 98.7 | 1.01 |
| | Example 6 | 0 | Light yellow-green clear liquid | 7.7 | 100.0 | 0.41 |
| | | 5 | Light yellow-green clear liquid | 7.7 | 99.7 | 0.49 |
| | | 10 | Light yellow-green clear liquid | 7.7 | 99.6 | 0.56 |
| | Example 7 | 0 | Light yellow-green clear liquid | 7.7 | 100.0 | 0.41 |
| | | 5 | Light yellow-green clear liquid | 7.7 | 99.5 | 0.54 |
| | | 10 | Light yellow-green clear liquid | 7.7 | 99.1 | 0.70 |
| | Example 8 | 0 | Light yellow-green clear liquid | 7.7 | 100.0 | 0.41 |
| | | 5 | Light yellow-green clear liquid | 7.7 | 99.8 | 0.50 |
| | | 10 | Light yellow-green clear liquid | 7.7 | 99.6 | 0.58 |
| | Example 9 | 0 | Light yellow-green clear liquid | 7.7 | 100.0 | 0.41 |
| | | 5 | Light yellow-green clear liquid | 7.7 | 99.6 | 0.53 |
| | | 10 | Light yellow-green clear liquid | 7.7 | 99.3 | 0.62 |
| | Example 10 | 0 | Light yellow-green clear liquid | 7.7 | 100.0 | 0.41 |
| | | 5 | Light yellow-green clear liquid | 7.7 | 99.5 | 0.48 |
| | | 10 | Light yellow-green clear liquid | 7.7 | 99.4 | 0.57 |
| | Example 11 | 0 | Light yellow-green clear liquid | 7.7 | 100.0 | 0.41 |
| | | 5 | Light yellow-green clear liquid | 7.7 | 98.6 | 0.91 |
| | | 10 | Light yellow-green clear liquid | 7.7 | 98.4 | 1.18 |
| | Example 12 | 0 | Light yellow-green clear liquid | 7.7 | 100.0 | 0.40 |
| | | 5 | Light yellow-green clear liquid | 7.7 | 99.6 | 0.54 |
| | | 10 | Light yellow-green clear liquid | 7.7 | 99.2 | 0.58 |
| | Comparative Example 1 | 0 | Light yellow-green clear liquid | 7.7 | 100.0 | 0.41 |
| | | 5 | Light yellow-green clear liquid | 7.7 | 98.2 | 1.16 |
| | | 10 | Light yellow-green clear liquid | 7.7 | 97.3 | 2.24 |
| | Comparative Example 2 | 0 | Light yellow-green clear liquid | 7.7 | 100.0 | 0.41 |
| | | 5 | Light yellow-green clear liquid | 7.7 | 97.8 | 1.48 |
| | | 10 | Light yellow-green clear liquid | 7.7 | 96.5 | 2.73 |

2. Accelerated Test

The meloxicam eye drops prepared in above Examples and Comparative Examples were taken and placed in colorless, transparent and sealed ampoules, stored under the condition of a temperature of 40° C.±2° C. and RH75%±5% for 6 months, sampled for inspection in 1st, 2nd, 3rd and 6th month, the results were compared with those from the 0th day sample, the test results are shown in Table 7:

TABLE 7

The accelerated test results of meloxicam eye drops

| Condition | Sample | Time (month) | Appearance | pH value | Content (%) | Related substances % |
|---|---|---|---|---|---|---|
| 40° C. ± 2° C. RH75% ± 5% | Example 1 | 0 | Light yellow-green clear liquid | 7.7 | 100.0 | 0.41 |
| | | 1 | Light yellow-green clear liquid | 7.7 | 99.3 | 0.74 |
| | | 2 | Light yellow-green clear liquid | 7.7 | 98.8 | 0.89 |
| | | 3 | Light yellow-green clear liquid | 7.7 | 97.2 | 1.15 |
| | | 6 | Light yellow-green clear liquid | 7.7 | 96.8 | 1.58 |
| | Example 2 | 0 | Light yellow-green clear liquid | 7.7 | 100.0 | 0.41 |
| | | 1 | Light yellow-green clear liquid | 7.7 | 99.5 | 0.57 |
| | | 2 | Light yellow-green clear liquid | 7.7 | 99.1 | 0.68 |
| | | 3 | Light yellow-green clear liquid | 7.7 | 98.5 | 0.97 |
| | | 6 | Light yellow-green clear liquid | 7.7 | 97.2 | 1.26 |
| | Example 3 | 0 | Light yellow-green clear liquid | 7.7 | 100.0 | 0.41 |
| | | 1 | Light yellow-green clear liquid | 7.7 | 99.6 | 0.48 |
| | | 2 | Light yellow-green clear liquid | 7.7 | 98.9 | 0.75 |
| | | 3 | Light yellow-green clear liquid | 7.7 | 98.0 | 1.01 |
| | | 6 | Light yellow-green clear liquid | 7.7 | 97.5 | 1.32 |
| | Example 4 | 0 | Light yellow-green clear liquid | 7.7 | 100.0 | 0.41 |
| | | 1 | Light yellow-green clear liquid | 7.7 | 99.5 | 0.55 |
| | | 2 | Light yellow-green clear liquid | 7.7 | 98.3 | 0.89 |
| | | 3 | Light yellow-green clear liquid | 7.7 | 97.6 | 1.23 |
| | | 6 | Light yellow-green clear liquid | 7.7 | 96.1 | 1.64 |
| | Example 5 | 0 | Light yellow-green clear liquid | 7.7 | 100.0 | 0.41 |
| | | 1 | Light yellow-green clear liquid | 7.7 | 99.3 | 0.51 |
| | | 2 | Light yellow-green clear liquid | 7.7 | 98.6 | 0.69 |
| | | 3 | Light yellow-green clear liquid | 7.7 | 98.1 | 0.98 |
| | | 6 | Light yellow-green clear liquid | 7.7 | 97.3 | 1.19 |
| | Example 6 | 0 | Light yellow-green clear liquid | 7.7 | 100.0 | 0.41 |
| | | 1 | Light yellow-green clear liquid | 7.7 | 99.8 | 0.45 |
| | | 2 | Light yellow-green clear liquid | 7.7 | 99.6 | 0.52 |
| | | 3 | Light yellow-green clear liquid | 7.7 | 99.5 | 0.55 |
| | | 6 | Light yellow-green clear liquid | 7.7 | 99.2 | 0.63 |
| | Example 7 | 0 | Light yellow-green clear liquid | 7.7 | 100.0 | 0.41 |
| | | 1 | Light yellow-green clear liquid | 7.7 | 99.8 | 0.49 |
| | | 2 | Light yellow-green clear liquid | 7.7 | 99.6 | 0.53 |
| | | 3 | Light yellow-green clear liquid | 7.7 | 99.0 | 0.67 |
| | | 6 | Light yellow-green clear liquid | 7.7 | 98.4 | 0.89 |
| | Example 8 | 0 | Light yellow-green clear liquid | 7.7 | 100.0 | 0.41 |
| | | 1 | Light yellow-green clear liquid | 7.7 | 99.8 | 0.45 |
| | | 2 | Light yellow-green clear liquid | 7.7 | 99.8 | 0.51 |
| | | 3 | Light yellow-green clear liquid | 7.7 | 99.6 | 0.53 |
| | | 6 | Light yellow-green clear liquid | 7.7 | 99.4 | 0.62 |
| | Example 9 | 0 | Light yellow-green clear liquid | 7.7 | 100.0 | 0.41 |
| | | 1 | Light yellow-green clear liquid | 7.7 | 99.9 | 0.46 |
| | | 2 | Light yellow-green clear liquid | 7.7 | 99.7 | 0.48 |
| | | 3 | Light yellow-green clear liquid | 7.7 | 99.4 | 0.52 |
| | | 6 | Light yellow-green clear liquid | 7.7 | 99.3 | 0.59 |
| | Example 10 | 0 | Light yellow-green clear liquid | 7.7 | 100.0 | 0.41 |
| | | 1 | Light yellow-green clear liquid | 7.7 | 99.8 | 0.43 |
| | | 2 | Light yellow-green clear liquid | 7.7 | 99.6 | 0.42 |
| | | 3 | Light yellow-green clear liquid | 7.7 | 99.4 | 0.55 |
| | | 6 | Light yellow-green clear liquid | 7.7 | 99.0 | 0.62 |
| | Example 11 | 0 | Light yellow-green clear liquid | 7.7 | 100.0 | 0.41 |
| | | 1 | Light yellow-green clear liquid | 7.7 | 99.5 | 0.68 |
| | | 2 | Light yellow-green clear liquid | 7.7 | 98.6 | 0.84 |
| | | 3 | Light yellow-green clear liquid | 7.7 | 98.3 | 1.05 |
| | | 6 | Light yellow-green clear liquid | 7.7 | 97.4 | 1.25 |
| | Example 12 | 0 | Light yellow-green clear liquid | 7.7 | 100.0 | 0.43 |
| | | 1 | Light yellow-green clear liquid | 7.7 | 99.8 | 0.52 |
| | | 2 | Light yellow-green clear liquid | 7.7 | 99.6 | 0.56 |
| | | 3 | Light yellow-green clear liquid | 7.7 | 99.2 | 0.61 |
| | | 6 | Light yellow-green clear liquid | 7.7 | 99.1 | 0.63 |
| | Comparative Example 1 | 0 | Light yellow-green clear liquid | 7.7 | 100.0 | 0.41 |
| | | 1 | Light yellow-green clear liquid | 7.7 | 99.7 | 0.79 |
| | | 2 | Light yellow-green clear liquid | 7.7 | 97.6 | 0.94 |
| | | 3 | Light yellow-green clear liquid | 7.7 | 96.3 | 1.46 |
| | | 6 | Light yellow-green clear liquid | 7.7 | 94.1 | 1.96 |

TABLE 7-continued

The accelerated test results of meloxicam eye drops

| Condition | Sample | Time (month) | Appearance | pH value | Content (%) | Related substances % |
|---|---|---|---|---|---|---|
| | Comparative Example 2 | 0 | Light yellow-green clear liquid | 7.7 | 100.0 | 0.41 |
| | | 1 | Light yellow-green clear liquid | 7.7 | 98.7 | 0.87 |
| | | 2 | Light yellow-green clear liquid | 7.7 | 96.2 | 1.26 |
| | | 3 | Light yellow-green clear liquid | 7.7 | 94.5 | 1.54 |
| | | 6 | Light yellow-green clear liquid | 7.7 | 92.1 | 2.23 |

3. Long-Term Test

The meloxicam eye drops prepared in above Examples and Comparative Examples were taken and placed in colorless, transparent and sealed ampoules, stored under the condition of a temperature of 25° C.±2° C. and RH60%±10% for 12 months, sampled for inspection in 3rd, 6th, 9th and 12th month, the results were compared with those from the 0th day sample, the test results are shown in Table 8:

TABLE 8

The long-term test results of meloxicam eye drops

| Condition | Sample | Time (month) | Appearance | pH value | Content (%) | Related substances % |
|---|---|---|---|---|---|---|
| 25° C. ± 2° C. RH60% ± 10% | Example 1 | 0 | Light yellow-green clear liquid | 7.7 | 100.7 | 0.11 |
| | | 3 | Light yellow-green clear liquid | 7.7 | 100.2 | 0.27 |
| | | 6 | Light yellow-green clear liquid | 7.7 | 99.5 | 0.45 |
| | | 9 | Light yellow-green clear liquid | 7.7 | 98.3 | 0.58 |
| | | 12 | Light yellow-green clear liquid | 7.7 | 97.8 | 0.79 |
| | Example 2 | 0 | Light yellow-green clear liquid | 7.7 | 100.8 | 0.13 |
| | | 3 | Light yellow-green clear liquid | 7.7 | 100.2 | 0.28 |
| | | 6 | Light yellow-green clear liquid | 7.7 | 99.9 | 0.44 |
| | | 9 | Light yellow-green clear liquid | 7.7 | 99.3 | 0.66 |
| | | 12 | Light yellow-green clear liquid | 7.7 | 98.6 | 0.72 |
| | Example 3 | 0 | Light yellow-green clear liquid | 7.7 | 100.9 | 0.10 |
| | | 3 | Light yellow-green clear liquid | 7.7 | 100.3 | 0.27 |
| | | 6 | Light yellow-green clear liquid | 7.7 | 99.6 | 0.42 |
| | | 9 | Light yellow-green clear liquid | 7.7 | 99.2 | 0.53 |
| | | 12 | Light yellow-green clear liquid | 7.7 | 98.3 | 0.75 |
| | Example 4 | 0 | Light yellow-green clear liquid | 7.7 | 100.5 | 0.13 |
| | | 3 | Light yellow-green clear liquid | 7.7 | 100.3 | 0.27 |
| | | 6 | Light yellow-green clear liquid | 7.7 | 99.4 | 0.35 |
| | | 9 | Light yellow-green clear liquid | 7.7 | 98.5 | 0.61 |
| | | 12 | Light yellow-green clear liquid | 7.7 | 97.6 | 0.84 |
| | Example 5 | 0 | Light yellow-green clear liquid | 7.7 | 100.6 | 0.11 |
| | | 3 | Light yellow-green clear liquid | 7.7 | 100.0 | 0.27 |
| | | 6 | Light yellow-green clear liquid | 7.7 | 99.6 | 0.44 |
| | | 9 | Light yellow-green clear liquid | 7.7 | 99.1 | 0.53 |
| | | 12 | Light yellow-green clear liquid | 7.7 | 98.7 | 0.72 |
| | Example 6 | 0 | Light yellow-green clear liquid | 7.7 | 100.7 | 0.11 |
| | | 3 | Light yellow-green clear liquid | 7.7 | 100.5 | 0.15 |
| | | 6 | Light yellow-green clear liquid | 7.7 | 100.2 | 0.22 |
| | | 9 | Light yellow-green clear liquid | 7.7 | 100.0 | 0.25 |
| | | 12 | Light yellow-green clear liquid | 7.7 | 99.8 | 0.29 |
| | Example 7 | 0 | Light yellow-green clear liquid | 7.7 | 100.5 | 0.11 |
| | | 3 | Light yellow-green clear liquid | 7.7 | 100.3 | 0.28 |
| | | 6 | Light yellow-green clear liquid | 7.7 | 100.2 | 0.40 |
| | | 9 | Light yellow-green clear liquid | 7.7 | 99.9 | 0.46 |
| | | 12 | Light yellow-green clear liquid | 7.7 | 99.0 | 0.53 |
| | Example 8 | 0 | Light yellow-green clear liquid | 7.7 | 100.6 | 0.11 |
| | | 3 | Light yellow-green clear liquid | 7.7 | 100.5 | 0.17 |
| | | 6 | Light yellow-green clear liquid | 7.7 | 100.2 | 0.28 |
| | | 9 | Light yellow-green clear liquid | 7.7 | 99.8 | 0.30 |
| | | 12 | Light yellow-green clear liquid | 7.7 | 99.7 | 0.33 |
| | Example 9 | 0 | Light yellow-green clear liquid | 7.7 | 100.8 | 0.10 |
| | | 3 | Light yellow-green clear liquid | 7.7 | 100.6 | 0.16 |
| | | 6 | Light yellow-green clear liquid | 7.7 | 100.5 | 0.19 |
| | | 9 | Light yellow-green clear liquid | 7.7 | 100.2 | 0.22 |
| | | 12 | Light yellow-green clear liquid | 7.7 | 99.8 | 0.27 |
| | Example 10 | 0 | Light yellow-green clear liquid | 7.7 | 100.6 | 0.10 |
| | | 3 | Light yellow-green clear liquid | 7.7 | 100.5 | 0.18 |
| | | 6 | Light yellow-green clear liquid | 7.7 | 100.3 | 0.21 |
| | | 9 | Light yellow-green clear liquid | 7.7 | 100.2 | 0.24 |
| | | 12 | Light yellow-green clear liquid | 7.7 | 99.6 | 0.31 |

TABLE 8-continued

The long-term test results of meloxicam eye drops

| Condition | Sample | Time (month) | Appearance | pH value | Content (%) | Related substances % |
|---|---|---|---|---|---|---|
| | Example 11 | 0 | Light yellow-green clear liquid | 7.7 | 100.4 | 0.10 |
| | | 3 | Light yellow-green clear liquid | 7.7 | 100.0 | 0.20 |
| | | 6 | Light yellow-green clear liquid | 7.7 | 99.8 | 0.41 |
| | | 9 | Light yellow-green clear liquid | 7.7 | 99.4 | 0.48 |
| | | 12 | Light yellow-green clear liquid | 7.7 | 98.7 | 0.77 |
| | Example 12 | 0 | Light yellow-green clear liquid | 7.7 | 100.5 | 0.10 |
| | | 3 | Light yellow-green clear liquid | 7.7 | 100.3 | 0.12 |
| | | 6 | Light yellow-green clear liquid | 7.7 | 100.0 | 0.17 |
| | | 9 | Light yellow-green clear liquid | 7.7 | 99.7 | 0.20 |
| | | 12 | Light yellow-green clear liquid | 7.7 | 99.6 | 0.26 |
| | Comparative Example 1 | 0 | Light yellow-green clear liquid | 7.7 | 100.4 | 0.10 |
| | | 3 | Light yellow-green clear liquid | 7.7 | 99.9 | 0.35 |
| | | 6 | Light yellow-green clear liquid | 7.7 | 99.0 | 0.49 |
| | | 9 | Light yellow-green clear liquid | 7.7 | 97.2 | 0.88 |
| | | 12 | Light yellow-green clear liquid | 7.7 | 95.8 | 1.23 |
| | Comparative Example 2 | 0 | Light yellow-green clear liquid | 7.7 | 100.4 | 0.17 |
| | | 3 | Light yellow-green clear liquid | 7.7 | 99.2 | 0.39 |
| | | 6 | Light yellow-green clear liquid | 7.7 | 97.3 | 0.52 |
| | | 9 | Light yellow-green clear liquid | 7.7 | 95.2 | 0.99 |
| | | 12 | Light yellow-green clear liquid | 7.7 | 94.1 | 1.32 |

Conclusion: The samples of Comparative Examples and Examples were stored under the conditions of a temperature of 40° C.±2° C., RH75%±5% and a temperature of 25° C.±2° C., RH60%±10% separately for 6 months and 12 months, respectively. Comparing with the eye drops without solubilizer or water-soluble polymer material, the eye drops containing hydroxypropyl-β-cyclodextrin and water-soluble polymer material like sodium hyaluronate, hydroxypropyl methyl cellulose were more stable. The results show that, with the incorporation of hydroxypropyl-β-cyclodextrin and water-soluble polymer material in the formulation of meloxicam eye drops, the stability of the drug was greatly improved, the stability of meloxicam eye drops in long-term storage was also improved, the risk of drug was reduced, the safety of the drug was enhanced.

The anti-inflammatory effect of topical application of 0.025%, 0.05%, 0.1% meloxicam eye drops were evaluated by rabbit eye anterior chamber puncture test and irritation test of ocular topical administration. The results indicate that, meloxicam eye drops could significantly inhibit the increase in protein concentration of the rabbit eye aqueous humor caused by puncture of the anterior chamber; single dose or continuous administration for 7 days have no irritation; haemolysis and blood cell aggregation phenomenon were not observed in the meloxicam eye drops in vitro haemolysis test; in meloxicam eye drops guinea pig eye allergy test, allergic reaction was not observed.

1. Rabbit Eye Anterior Chamber Puncture Test

Thirty-six rabbits without ocular abnormalities were taken and randomly divided into six groups, with six rabbits in each group. The groups are respectively saline group, medium control group, positive control group of diclofenac sodium, 0.025%, 0.05% and 0.1% meloxicam eye drops groups. Then 0.05 mL drug solution was dropped into the rabbit eyes for experiment. The eyes were forced to be closed for 10 seconds; 45 minutes later, under local anesthesia with 0.2 mL of 1% tetracaine drops, puncturing was performed with 41/2 needle from the edge of the limbus to take 0.2 mL of primary aqueous humor; 90 minutes later, puncturing was performed again to take the secondary aqueous humor. Those two batches of aqueous humor were diluted 2-fold and 50-fold respectively. Then 0.05 mL of distilled water, aqueous humor dilution and protein standard solution were taken, 3 mL Coomassie brilliant blue staining solution was added thereto respectively, after 10 minutes of reaction, their absorbance values at 595 nm were measured, and the protein content was calculated according to the following formula:

$$\text{Measuring tube protein content (mg/ml)} = \frac{\text{Measuring tube absorbance}}{\text{Standard tube absorbance}} \times \text{Standard tube protein content (mg/ml)}$$

The results show that, both meloxicam eye drops and diclofenac sodium eye drops could significantly inhibit the increase in aqueous humor protein concentration caused by the puncture of anterior chamber. There are significant differences as compared with the saline group and medium control group, see Table 9.

TABLE 9

The inhibitory effect of meloxicam eye drops on the increase of aqueous humor protein concentration caused by puncture of anterior chamber ($\bar{x} \pm s$).

| Group | n | Dose (ml/eye) | Protein concentration in aqueous humor (mg/ml) | |
|---|---|---|---|---|
| | | | Primary | Secondary |
| Saline | 6 | 0.05 | 0.69 ± 0.19 | 35.19 ± 8.10 |
| Medium control | 6 | 0.05 | 0.65 ± 0.19 | 34.50 ± 8.73 |
| Diclofenac sodium | 6 | 0.05 | 0.52 ± 0.19 | 18.05 ± 3.01**ΔΔ |
| Meloxicam 0.025% | 6 | 0.05 | 0.56 ± 0.21 | 24.60 ± 5.93*Δ |
| Meloxicam 0.05% | 6 | 0.05 | 0.45 ± 0.14* | 22.82 ± 4.01**Δ |
| Meloxicam 0.1% | 6 | 0.05 | 0.43 ± 0.13*Δ | 16.56 ± 3.48**ΔΔ |

Comparing with the saline group,
*P < 0.05;
**P < 0.01
Comparing with the medium control group,
ΔP < 0.05;
ΔΔP < 0.01

Through the experiment it can be concluded that meloxicam has significant inhibitory effect on the increase of aqueous humor protein concentration caused by the puncture on the rabbit eye anterior chamber. It also has therapeutic effect on non-bacterial ocular inflammation; the action intensity is similar with that of diclofenac sodium eye drops, while the effects appear faster.

2. Irritation Test for Ocular Topical Administration 2.1 Single-Dose Irritation Test Sixteen rabbits without ocular abnormalities were taken and randomly divided into 4 groups, with 4 rabbits in each group. Groups 1-3 were the experimental groups, and group 4 was the medium control group. Into the right eyes of the rabbits in each group, 0.1 mL of 0.025%, 0.05%, 0.1% meloxicam eye drops were dropped, and in blank control group 0.1 mL blank medium was dropped. Into all the left eyes were dropped the same volume of saline as control. The eyes were forced to be closed for about 10 s. Irritation within 6 hours was observed, and 24, 48, 72 hours after administration, irritation was observed again. The eye irritation response was scored according to the assessment scale from literature as shown in Table 10, and recorded.

The irritation response scores of the animals' cornea, iris and conjunctiva after contact with the test samples are summed up to get the final total score of irritation response for each test sample; the total score is divided by the number of animals to get the final eye irritation score for each animal. Based on the highest score, the degree of irritation is evaluated according to the assessment scale shown in Table 11. The results are shown in Table 12.

2.2 Irritation of Continuous Medication for 7 Days and Irritation Experiment One Week after Drug Withdrawal Sixteen rabbits were taken and checked for none ocular abnormalities, and randomly divided into four groups, with 4 rabbits in each group. The groups are blank control group, 0.025%, 0.05% and 0.1% meloxicam eye drops groups respectively. Meloxicam with each concentration and blank medium were dropped into the conjunctival sac in the dosage of 0.1 nil. Saline was dropped into the other side as control. The eye lids were forced to be closed for about 10 s. The drug was administered every morning, and the animals were observed for 6 hours, scored, continued for a week. The score was determined according to the standard above, and the irritation intensity was judged. The experimental results of irritation intensity are shown in Table 13.

From Table 12, Table 13 the mild, barely visible vasodilation effect can be observed on the sclera after drug administration. All the scores are less than 3 points, which indicates the absence of irritation. No toxic response was observed after drug withdrawal.

TABLE 10

Eye stimulus response score.

| Eye irritation response | Scores |
|---|---|
| Corneal opacity (based on the most compact part.) | |
|    No opacity | 0 |
|    Sporadic or diffuse opacities, iris clearly visible | 1 |
|    Translucent area can be easily identified, blurry iris | 2 |
|    Existence of gray translucent region, the fine structure of the iris is unclear, pupil size barely visible | 3 |
|       Opaque cornea; iris is illegible due to the opacity | 4 |
|    Normal iris | 0 |
|    Folds deepen, hyperemia, swelling, mild hyperemia around the cornea, the pupil may still respond to light | 1 |
|    Hemorrhage, necrosis can be observed with naked eyes, no response to light (or one of the pathological reaction) | 2 |
| Conjunctiva | |
| A.  Hyperemia (refers to the palpebral conjunctiva and the bulbar conjunctiva parts) | |
|    Normal vessel | 0 |
|    Vascular congestion, bright red | 1 |
|    Vascular congestion appears dark red, vessels cannot be easily identified | 2 |
|    Diffuse hyperemia, appears purple | 3 |
| B.  Edema | |
|    No edema | 0 |
|    Slight edema (including nictitating membrane) | 1 |
|    Obvious edema, accompanied with partial conjunctival eversion | 2 |
|    Edema leads to nearly half closure of the eyelid | 3 |
|    Edema leads to more than half closure of the eyelid | 4 |
| C.  Secretion | |
|    No secretion | 0 |
|    Small amount of secretion | 1 |
|    Secretion makes the eyelids and eyelashes moist or sticky | 2 |
|    Secretion makes the entire eye region moist or sticky | 3 |

Note:
This drug has mild, barely visible and transient vasodilatory effect, recorded as 0.5 points.

TABLE 11

Eye irritation evaluation criteria

| Degree of irritation | Total score |
|---|---|
| No irritation | 0-3 |
| Mild irritation | 4-8 |
| Moderate irritation | 9-12 |
| Strong irritation | 13-16 |

TABLE 12

Irritation to the conjunctiva in single dose (n = 4)

| Group | Dosage (ml) | 6 h | 24 h | 48 h | 72 h | Irritation intensity |
|---|---|---|---|---|---|---|
| NS | 0.1 | 0 | 0 | 0 | 0 | — |
| Excipient | 0.1 | 0.13 | 0 | 0 | 0 | — |

TABLE 12-continued

Irritation to the conjunctiva in single dose (n = 4)

| Group | Dosage (ml) | Irritation score | | | | Irritation intensity |
|---|---|---|---|---|---|---|
| | | 6 h | 24 h | 48 h | 72 h | |
| 0.025% meloxicam | 0.1 | 0.13 | 0 | 0 | 0 | — |
| 0.05% meloxicam | 0.1 | 0.13 | 0 | 0 | 0 | — |
| 0.1% meloxicam | 0.1 | 0.25 | 0 | 0 | 0 | — |

(—) Indicates no irritation, as determined with the irritation intensity assessment scale.

TABLE 13

Irritation after 7-day continuous administration and the irritation response one week after drug withdrawal

| Group | Irritation score after administration | | | | | | | Irritation intensity | Irritation after drug withdrawal 8~14 (d) |
|---|---|---|---|---|---|---|---|---|---|
| | 1 | 2 | 3 | 4 | 5 | 6 | 7 (d) | | |
| NS | 0 | 0 | 0 | 0 | 0 | 0 | 0 | — | 0 |
| Excipient | 0.25 | 0.25 | 0.25 | 0.5 | 0 | 0 | 0 | — | 0 |
| 0.025% meloxicam | 0.13 | 0.25 | 0.5 | 0.5 | 0.25 | 0.25 | 0.25 | — | 0 |
| 0.05% meloxicam | 0.25 | 0.5 | 0.25 | 0.25 | 0.5 | 0.25 | 0.5 | — | 0 |
| 0.1% meloxicam | 0.25 | 0.45 | 0.5 | 0.5 | 0.5 | 0.5 | 0.25 | — | 0 |

(—) Indicates no irritation, as determined with the irritation intensity assessment scale.

2.3 In Vitro Hemolysis Test

Blood was taken from the ear vein of the rabbit. According to the method described in the literature, the fibrin was removed through stirring with bamboo sticks. The samples were washed with saline and centrifuged, the process was repeated several times until no red color is observed from the supernatant. The samples were reconstituted with saline to make 2.0% (v/v) erythrocyte suspension for the tests.

Take 7 test tubes. Various volumes of drug solution and erythrocyte suspension were added into the tubes as shown in Table 14. In Tube 6, no drug was added, while saline was added as blank control. Distilled water was added into Tube 7 as complete hemolysis control. Mixed gently, all the tubes were kept in 37° C. water bath for 4 hrs, and recorded every one hour for totally 4 times. The presence/absence of hemolysis was observed with naked eyes according to the standards described in the literature. After the final observation, the tubes were sufficiently shaked, and the presence/absence of precipitation and aggregation was observed. The results are shown in Table 14.

TABLE 14

Hemolysis test for meloxicam eye drops

| | Tube No. | | | | | | |
|---|---|---|---|---|---|---|---|
| | 1 | 2 | 3 | 4 | 5 | 6 | 7 |
| Test sample (ml) | 0.1 | 0.2 | 0.3 | 0.4 | 0.5 | 0 | Distilled water 2.5 |
| Saline (ml) | 2.4 | 2.3 | 2.2 | 2.1 | 2.0 | 2.5 | 0 |
| 2.0% erythrocyte suspension | 2.5 | 2.5 | 2.5 | 2.5 | 2.5 | 2.5 | 2.5 |
| Hemolysis | − | − | − | − | − | − | ++ |

Judge:
(−) Indicates no hemolysis, no aggregation, no precipitation reactions.
(+) Indicates partial hemolysis.
(++) Indicates complete hemolysis.

In the in vitro hemolysis test of 0.1% meloxicam eye drops, neither hemolysis nor blood cell aggregation was observed. Comparing with saline group, no significant difference was found. Distilled water group showed complete hemolysis, resulting in red transparent solution.

2.4 Allergy Test for Topical Administration

Thirty guinea pigs, with half male and half female, were taken and randomly divided into three groups, with 10 pigs in each group. In the experimental group, 0.05 mL of 0.1% meloxicam was dropped into the conjunctival sac of the left eye; in the control group, 0.05 mL NS and medium solution are separately dropped in 3 consecutive days, drug was administered once a day; then, 7 and 14 days after the first administration, the drops were applied again. Twenty-eight days later, 0.05 mL drug was dropped at the conjunctiva of the right eye for challenge. The presence/absence of allergic reaction, and the severity of the allergic reaction were observed 6 hr, 24 hr, 48 hr and 72 hr after administration. The allergenicity rate was calculated, while the rating and judgement were performed according to the assessment scale for skin allergic reaction shown in Table 15. The results are shown in Table 16, no allergic reaction is observed in the topical administration within the eyes.

TABLE 15

Rating criteria for skin allergic reaction

| Skin reactions | Score |
|---|---|
| Erythema formation: | |
| No erythema | 0 |
| Mild erythema | 1 |
| Moderate erythema | 2 |
| Severe erythema | 3 |
| Edematous erythema | 4 |
| Edema formation: | |
| No edema | 0 |
| Mild edema | 1 |
| Moderate edema | 2 |
| Severe edema | 3 |
| Total Points | 7 |

Experiment conclusion: Meloxicam eye drops irritation test of the single-dose or continuous administration for 7 days of meloxicam eye drops on rabbits reveals no irritation; the phenomenon of hemolysis or blood cell aggregation is not observed from the in vitro hemolysis test for meloxicam eye drops; allergic reaction is not observed in the guinea pig eye allergy test for meloxicam eye drops.

TABLE 16

| Group | Number of animals | 6 h Allergic reaction score | 24 h Allergic reaction score | 48 h Allergic reaction score | 72 h Allergic reaction score |
|---|---|---|---|---|---|
| Meloxicam | 10 | 0 | 0 | 0 | 0 |
| Medium | 10 | 0 | 0 | 0 | 0 |
| NS | 10 | 0 | 0 | 0 | 0 |

The invention claimed is:

1. A meloxicam eyedrop, characterized in that, the meloxicam eyedrop comprises active ingredient meloxicam or a pharmaceutically acceptable salt thereof, a solubilizer, a stabilizer, a pH regulator, an osmotic pressure regulator and optionally a bacteriostatic agent, wherein the solubilizer is selected from the group consisting of hydroxypropyl-β-cyclodextrin, sulfobutylether-β-cyclodextrin, and β-cyclodextrin or a mixture thereof; wherein the stabilizer is selected from the group consisting of sodium hyaluronate, and hydroxypropyl methyl cellulose or a mixture thereof; wherein the pH regulator is selected from the group consisting of hydrochloric acid, boric acid, borax, sodium dihydrogen phosphate, disodium hydrogen phosphate, potassium dihydrogen phosphate, citric acid, and sodium citrate or a mixture thereof; wherein the osmotic pressure regulator is selected from the group consisting of sodium chloride, potassium chloride, boric acid, borax, sodium sulfate, potassium sulfate, sodium nitrate, potassium nitrate, sodium acetate, mannitol, glycerol, propylene glycol, and glucose or a mixture thereof; and wherein the bacteriostatic agent is selected from the group consisting of methyl paraben, ethyl paraben, propyl paraben, butyl paraben, benzalkonium chloride, benzalkonium bromide, chlorhexidine acetate, phenylmercuric nitrate, and thimerosal or a mixture thereof.

2. The meloxicam eyedrop according to claim 1, characterized in that the pharmaceutically acceptable salt of meloxicam is diethylamine salt, methylglucamine salt, sodium salt, potassium salt or ammonium salt.

3. The meloxicam eyedrop according to claim 2, characterized in that the pharmaceutically acceptable salt of meloxicam is diethylamine salt.

4. The meloxicam eyedrop according to claim 1, characterized in that the meloxicam eye drop consists of the following components in terms of weight: meloxicam or a pharmaceutically acceptable salt thereof, 0.05%-2.0%; solubilizer, 1.0-10%; stabilizer, 0.1-10%; pH regulator, 0.1-8.0%; osmotic pressure regulator, 0.1-2.0%; bacteriostatic agent, 0-0.5%; and water for injection, 85-98%.

5. The meloxicam eyedrop according to claim 4, characterized in that the pH of meloxicam eye drop is 6.5-9.0.

6. The meloxicam eyedrop according to claim 5, characterized in that the meloxicam eye drop consists of the following component in terms of weight: meloxicam or a pharmaceutically acceptable salt thereof, 0.1%; solubilizer, 1.0-5%; and stabilizer, 0.1-2%.

7. A method of treating non-infectious ophthalmic inflammation in a subject thereof, comprising administering the meloxicam eyedrop of claim 1 to the subject.

8. The meloxicam eyedrop according to claim 5, characterized in that the pH of meloxicam eye drop is 7.5-8.5.

* * * * *